United States Patent [19]

Bundy

[11] 4,277,612

[45] Jul. 7, 1981

[54] ω-ARYL-9-DEOXY-9-METHYLENE-5,6-DIDEHYDRO-PGF$_1$ COMPOUNDS

[75] Inventor: Gordon L. Bundy, Portage, Mich.

[73] Assignee: The Upjohn Company, Kalamazoo, Mich.

[21] Appl. No.: 116,080

[22] Filed: Jan. 28, 1980

Related U.S. Application Data

[62] Division of Ser. No. 35,144, May 1, 1979.

[51] Int. Cl.$^3$ .............................................. C07C 177/00
[52] U.S. Cl. ....................................... 560/55; 560/61; 560/62; 560/63; 562/471; 562/472; 260/408; 260/410; 260/410.5; 260/410.6; 260/413
[58] Field of Search ....................... 560/55, 61, 62, 63; 562/465, 472; 260/408, 410, 410.5, 410.6, 413

[56] References Cited

U.S. PATENT DOCUMENTS 4,118,584   10/1978   Bundy ................................... 560/55

*Primary Examiner*—Paul J. Killos
*Attorney, Agent, or Firm*—Robert A. Armitage

[57] ABSTRACT

The present invention particularly relates to novel ω-aryl-9-deoxy-9-methylene-5,6-didehydro-PFG$_1$ compounds and methods for their preparation in pharmacological use.

5 Claims, No Drawings

ω-ARYL-9-DEOXY-9-METHYLENE-5,6-DIDEHYDRO-PGF$_1$ COMPOUNDS

CROSS REFERENCE TO RELATED APPLICATIONS

The present application is a divisional application of U.S. Ser. No. 035,144, filed May 1, 1979, now pending.

BACKGROUND OF THE INVENTION

The present invention particularly relates to novel ω-aryl-9-deoxy-9-methylene-5,6-didehydro-PGF$_1$ compounds and methods for their preparation and pharmalogical use.

The essential material constituting the disclosure of the preparation and pharmacological use of the compounds of the present invention is incorporated here by reference from U.S. Ser. No. 035,144 and U.S. Pat. No. 4,060,534. The latter patent describes certain 9-deoxy-9-methylene-PGF-type compounds which are cis isomers of the novel compounds disclosed herein.

PRIOR ART

Known in the art are trans-5,6-didehydro PG$_1$ compounds and 9-deoxy-9-methylene PGF compounds. Trans-5,6-didehydro prostaglandins are described in U.S. Pat. Nos. 3,759,978, 3,823,180, 3,832,379, and 3,821,291.

SUMMARY OF THE INVENTION

The present invention particularly provides:
a prostaglandin analog of formula VI

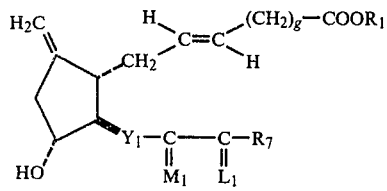

wherein Y$_1$ is trans—CH=CH—, —C≡C—, —CH$_2$CH$_2$—, or cis—CH=CH—;
wherein M$_1$ is α-R$_5$:β-OH or α-OH:β-R$_5$, wherein R$_5$ is hydrogen or methyl;
wherein L$_1$ is α-R$_3$:β-R$_4$, α-R$_4$:β-R$_3$, or a mixture of α-R$_3$:β-R$_4$ and α-R$_4$:β-R$_3$ wherein R$_3$ and R$_4$ are hydrogen, methyl, or fluoro, being the same or different, with the proviso that one of R$_3$ and R$_4$ is fluoro only when the other is hydrogen or fluoro;
wherein g is 3, 4, or 5;
wherein R$_7$ is
(1) phenoxy;
(2) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(3) phenyl;
(4) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(5) phenylmethyl, phenylethyl, or phenylpropyl;
(6) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that R$_7$ is phenoxy or substituted phenoxy only when R$_3$ and R$_4$ are hydrogen or methyl, being the same or different; and
wherein R$_1$ is
(a) hydrogen;
(b) alkyl of one to 12 carbon atoms, inclusive;
(c) cycloalkyl of 3 to 10 carbon atoms, inclusive;
(d) aralkyl of 7 to 12 carbon atoms, inclusive;
(e) phenyl;
(f) phenyl substituted with one, 2, or 3 chloro or alkyl of one to 3 carbon atoms;
(g) phenyl substituted in the para position by
  (i) —NH—CO—R$_{25}$
  (ii) —CO—R$_{26}$
  (iii) —O—CO—R$_{27}$
  (iv) —CH=N—NH—CO—NH$_2$
wherein R$_{25}$ is methyl, phenyl, acetamidophenyl, benzamidophenyl, or —NH$_2$; R$_{26}$ is hydroxy, methyl, phenyl, —NH$_2$, or methoxy; and R$_{27}$ is phenyl or acetamidophenyl; inclusive, or a pharmacologically acceptable salt thereof when R$_1$ is hydrogen.

DESCRIPTION OF THE PREFERRED EMBODIMENTS

The present invention particularly relates to the following specific embodiments:
5,6-trans-didehydro-9-deoxy-9-methylene-17-phenyl-18,19,20-trinor —PGF$_1$, and
5,6-trans-didehydro-9-deoxy-9-methylene-16-phenoxy-17,18,19,20-tetranor-PGF$_1$.

I claim:
1. A prostaglandin analog of formula VI

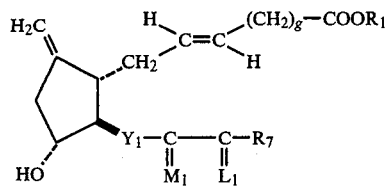

wherein Y$_1$ is trans—CH=CH—, —C≡C—, —CH$_2$CH$_2$—, or cis—CH=CH—;
wherein M$_1$ is α-R$_5$:β-OH or α-OH:R$_5$, wherein R$_5$ is hydrogen or methyl;
wherein L$_1$ is α-R$_3$:β-R$_4$, α-R$_4$:β-R$_3$, or a mixture of β-R$_3$:β-R$_4$ and α-R$_4$:β-R$_3$ wherein R$_3$ and R$_4$ are hydrogen, methyl, or fluoro, being the same or different, with the proviso that one of R$_3$ and R$_4$ is fluoro only when the other is hydrogen or fluoro;
wherein g is 3, 4, or 5;
wherein R$_7$ is
(1) phenoxy;
(2) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(3) phenyl;
(4) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;

(5) phenylmethyl, phenylethyl, or phenylpropyl;
(6) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy only when $R_3$ and $R_4$ are hydrogen or methyl, being the same or different; and wherein $R_1$ is
(a) hydrogen;
(b) alkyl of one to 12 carbon atoms, inclusive;
(c) cycloalkyl of 3 to 10 carbon atoms, inclusive;
(d) aralkyl of 7 to 12 carbon atoms, inclusive;
(e) phenyl;
(f) phenyl substituted with one, 2, or 3 chloro or alkyl of one to 3 carbon atoms;
(g) phenyl substituted in the para position by
  (i) —NH—CO—$R_{25}$
  (ii) —CO—$R_{26}$
  (iii) —O—CO—$R_{27}$
  (iv) —CH=N—NH—CO—NH$_2$
wherein $R_{25}$ is methyl, phenyl, acetamidophenyl, benzamidophenyl, or —NH$_2$; $R_{26}$ is hydroxy, methyl, phenyl, —NH$_2$, or methoxy; and $R_{27}$ is phenyl or acetamidophenyl; inclusive, or a pharmacologically acceptable salt thereof when $R_1$ is hydrogen.

2. A prostaglandin analog according to claim 1, wherein $R_7$ is phenyl or phenylalkyl or a substituted derivative thereof.

3. 5,6-trans-Didehydro-9-deoxy-9-methylene-17-phenyl-18,19,20-trinor-PGF$_1$, a prostaglandin analog according to claim 2.

4. A prostaglandin analog according to claim 1, wherein $R_7$ is phenoxy or substituted phenoxy.

5. 5,6-trans-Didehydro-9-deoxy-9-methylene-16-phenoxy-17,18,19,20-tetranor-PGF$_1$, a prostaglandin analog according to claim 4.

* * * * *

UNITED STATES PATENT OFFICE
CERTIFICATE OF CORRECTION

Patent No. 4,277,612     Dated 7 July 1981

Inventor(s) Gordon L. Bundy

It is certified that error appears in the above-identified patent and that said Letters Patent are hereby corrected as shown below:

In the Abstract, line 2, "PFG$_1$" should read -- PGF$_1$ --;

Column 1, line 9, "now pending" should read -- now U.S. Patent 4,220,796 --; line 18, "Serial No. 035,144" should read -- Patent No. 4,220,796 --; line 42, "-C=C-" should read -- -C≡C- --;

Column 2, line 45, "-C=C-" should read -- -C≡C- --.

Signed and Sealed this

Twenty-seventh Day of October 1981

[SEAL]

*Attest:*

*Attesting Officer*

GERALD J. MOSSINGHOFF

*Commissioner of Patents and Trademarks*